United States Patent [19]

Rich et al.

[11] Patent Number: 5,027,808
[45] Date of Patent: Jul. 2, 1991

[54] BREATH-ACTIVATED INHALATION DEVICE

[75] Inventors: Michael Rich, Newtown, Conn.; Paul Mulhauser; Douglas Spranger, both of New York, N.Y.

[73] Assignee: Tenax Corporation, Danbury, Conn.

[21] Appl. No.: 606,135

[22] Filed: Oct. 31, 1990

[51] Int. Cl.⁵ .............................................. A61M 15/08
[52] U.S. Cl. ........................ 128/203.23; 128/202.21; 128/203.12; 128/200.23
[58] Field of Search ................ 128/202.21, 203.23, 128/203.12; 222/635

[56] References Cited

U.S. PATENT DOCUMENTS

| | | | |
|---|---|---|---|
| 3,456,644 | 7/1969 | Thiel | 128/200.23 |
| 3,456,645 | 7/1969 | Brock | 128/200.23 |
| 3,456,646 | 7/1969 | Phillips et al. | 128/200.23 |
| 3,565,070 | 2/1971 | Hanson | 128/200.23 |
| 3,636,949 | 1/1972 | Kropp | 128/200.23 |
| 3,732,864 | 5/1973 | Thompson et al. | 128/200.23 |
| 3,764,046 | 10/1973 | Riccio | 222/635 |
| 3,785,530 | 1/1974 | Riccio | 222/635 |
| 3,788,525 | 1/1974 | Thornton et al. | 222/635 |
| 3,788,526 | 1/1974 | Thornton et al. | 222/635 X |
| 3,789,843 | 2/1974 | Armstrong et al. | 128/200.23 |
| 3,814,297 | 6/1974 | Warren | 222/402.13 |
| 3,818,908 | 6/1974 | Phillips | 604/301 |
| 3,826,413 | 7/1974 | Warren | 222/402 |
| 3,856,185 | 12/1974 | Riccio | 222/635 |
| 4,137,914 | 2/1979 | Wetterlin | 128/200.23 |
| 4,291,688 | 9/1981 | Kistler | 128/200.23 |
| 4,292,966 | 10/1981 | Mono et al. | 128/200.23 |
| 4,352,789 | 10/1982 | Thiel | 424/46 |
| 4,393,884 | 7/1983 | Jacobs | 131/273 |
| 4,414,972 | 11/1983 | Young et al. | 128/200.23 |
| 4,446,862 | 5/1984 | Baum et al. | 128/203.15 |
| 4,470,412 | 9/1984 | Nowacki et al. | 128/200.18 |
| 4,509,515 | 4/1985 | Altounyan et al. | 128/200.23 |
| 4,534,343 | 8/1985 | Nowacki et al. | 128/200.23 |
| 4,576,157 | 3/1986 | Rahusprasad | 128/200.23 |
| 4,592,348 | 6/1986 | Waters, IV et al. | 128/200.23 |
| 4,624,251 | 11/1986 | Miller | 128/200.14 |
| 4,635,627 | 1/1987 | Gam | 128/200.14 |
| 4,641,644 | 2/1987 | Andersson et al. | 128/200.23 |
| 4,648,393 | 3/1987 | Landis et al. | 128/200.23 |
| 4,664,107 | 5/1987 | Wass | 128/200.23 |
| 4,703,753 | 11/1987 | Bordoni et al. | 128/200.14 |
| 4,796,614 | 1/1989 | Nowacki et al. | 128/200.14 |
| 4,819,834 | 4/1989 | Thiel | 222/355 |
| 4,834,083 | 5/1989 | Byram et al. | 128/200.23 |
| 4,852,561 | 8/1989 | Sperry | 128/200.23 |
| 4,860,740 | 8/1989 | Kirk et al. | 128/203.15 |
| 4,896,832 | 1/1990 | Howlett | 222/95 X |
| 4,945,929 | 8/1990 | Egilmex | 128/202.21 X |

FOREIGN PATENT DOCUMENTS

| | | | |
|---|---|---|---|
| 960190 | 12/1974 | Canada | 222/635 |
| 1917911 | 10/1970 | Fed. Rep. of Germany . | |
| 1270272 | 4/1972 | United Kingdom . | |
| 2195544 | 4/1988 | United Kingdom | 128/203.12 |

*Primary Examiner*—Edgar S. Burr
*Assistant Examiner*—E. P. Raciti
*Attorney, Agent, or Firm*—Kramer, Brufsky & Cifelli

[57] ABSTRACT

Upon inhalation of air from the interior of a housing, a flexible diaphragm-type valve exposed to the ambient air surrounding the housing is moved inwardly due to the difference in ambient air pressure to that in the housing to expose the interior of the housing to the ambient air which is then drawn into the housing. Upon movement of the valve, it strikes a lever connected to a toggle linkage arrangement, causing the lever to pivot to break the toggle linkage, enabling a coil spring to extend and move downwardly a medicant-containing bottle relative to the valve stem of an aerosol valve. The valve stem is urged upwardly relative to a nozzle and moved into the interior of the bottle dispensing a metered dose of the medicant to be mixed with the inhaled air, which is inhaled by the user until the valve automatically closes by extension of the valve stem relative to the nozzle. The bottle is moved upwardly by a pushbutton to reset the toggle linkage actuation means and hold the bottle relative to the nozzle with its valve stem extended. Upward movement of the bottle cocks and resets the toggle linkage to a locked position precluding downward movement of the bottle until the inhalation cycle is repeated.

3 Claims, 3 Drawing Sheets

BREATH-ACTIVATED INHALATION DEVICE

BACKGROUND OF THE INVENTION

1. Field of the Invention

This invention relates to a device for dispensing a dose of a medicant, and more particularly, a medicant dispensing device which is activated by the user upon inhalation of air from the interior of the housing of the device.

2. Description of the Prior Art

U.S. Pat. Nos. 3,456,644; 3,456,646; 3,565,070; 3,636,949; 3,732,864; 3,789,843; 3,814,297; 3,826,413; 4,648,393; 4,664,107; and 4,648,393 all disclose a breath-activated inhalation device wherein a dose of a medicant is dispensed from an aerosol container to be mixed with air drawn into the housing of the inhalation device upon inhalation by a user. Each of these patents illustrate a device wherein the air drawn from the exterior of the housing upon inhalation by the user opens a valve and flows through an opening normally closed by the valve into the interior of the housing. Movement of the valve in turn causes movement of a linkage arrangement to permit the aerosol container to drop or be moved downwardly to open the aerosol valve of the container so that a measured dose of a medicant can be inhaled with the air entering the housing.

Perhaps the most analogous disclosure to that of the present invention is illustrated in U.S. Pat. No. 3,456,644. Upon inhalation, a valve 66 floats up sleeve 63 allowing air to enter a housing 22 through openings 65 and 62. The valve 66 strikes lever 51 causing it to rotate in a clockwise direction as viewed in FIGS. 2 and 3 of the drawings. The pivoting of the lever releases a pawl 53 from contact with a groove 54 on a block above the medicant-carrying container in the housing of the device, enabling a pair of springs 49,50 to extend, to push the block against the bottom of the container, causing it to move downwardly to open its aerosol valve, so that medicant can be dispensed into an air passage in the housing for inhalation with the air drawn into the housing from the exterior of the housing. The lever 51 is reset by pushing the medicant-carrying container back to a position wherein the pawl can reseat in the notch 54 to hold the container in a raised position. This is accomplished by exerting pressure on stem 43 to move the container upwardly relative to its aerosol valve to close the container.

While the inhalation-actuated aerosol dispensing device of U.S. Pat. No. 3,456,644 is structurally similar and does disclose the concepts involved in the present invention, the toggle linkage arrangement used in the present invention for holding the aerosol valve in its closed position by precluding the drop of medicant-containing bottle relative to the valve under the urging of the coil spring is different. In lieu of the pawl and notch arrangement, the present invention utilizes a toggle linkage so that when the arms of the linkage are aligned in a linear fashion, the force of the coil spring cannot urge the container to drop to open the aerosol valve. This lock linkage ensures activation of the device only upon inhalation by a user.

SUMMARY OF THE INVENTION

Upon inhalation of air from the interior of a housing, a flexible diaphragm-type valve exposed to the ambient air surrounding the housing is moved inwardly due to the difference in ambient air pressure to that in the housing to expose the interior of the housing to the ambient air which is then drawn into the housing. Upon movement of the valve, it strikes a lever connected to a toggle linkage arrangement, causing the lever to pivot to move the toggle linkage, enabling a first coil spring to extend and move a block against the rear of a medicant-containing, aerosol valve actuated, bottle. The bottle is urged downwardly by the block. As the bottle drops, an aerosol valve stem in the bottle pushes a floating nozzle downwardly against the bias of a second coil spring, and moves upwardly into the bottle, opening the valve, and dispensing a metered dose of the medicant to be mixed with the inhaled air, which combination is inhaled by the user. The nozzle causes the second coil spring to assure the extension of a pushbutton exteriorly of the housing as it reexpands. When the force on the extended valve stem by the nozzle under the urging of the second coil spring is insufficient to overcome the opposed force exerted by an internal spring forcing the valve stem out of the bottle, the aerosol valve closes by being extended exteriorly of the bottle, providing the metered dose of medicant. The pushbutton can be manually returned upwardly to recock and relock the device, and then the pushbutton returns to its normal outward position. The toggle linkage arrangement is reset to lock the first coil spring in a compressed condition until the inhalation cycle is repeated, while the lever is repivoted by the linkage to close the flexible diaphragm-type valve and the housing to the atmosphere.

BRIEF DESCRIPTION OF THE DRAWINGS

Further objects and advantages of the invention will become apparent from the following specification and claims, and from the accompanying drawings, wherein:

DETAILED DESCRIPTION OF THE PREFERRED EMBODIMENT

Figure 1:
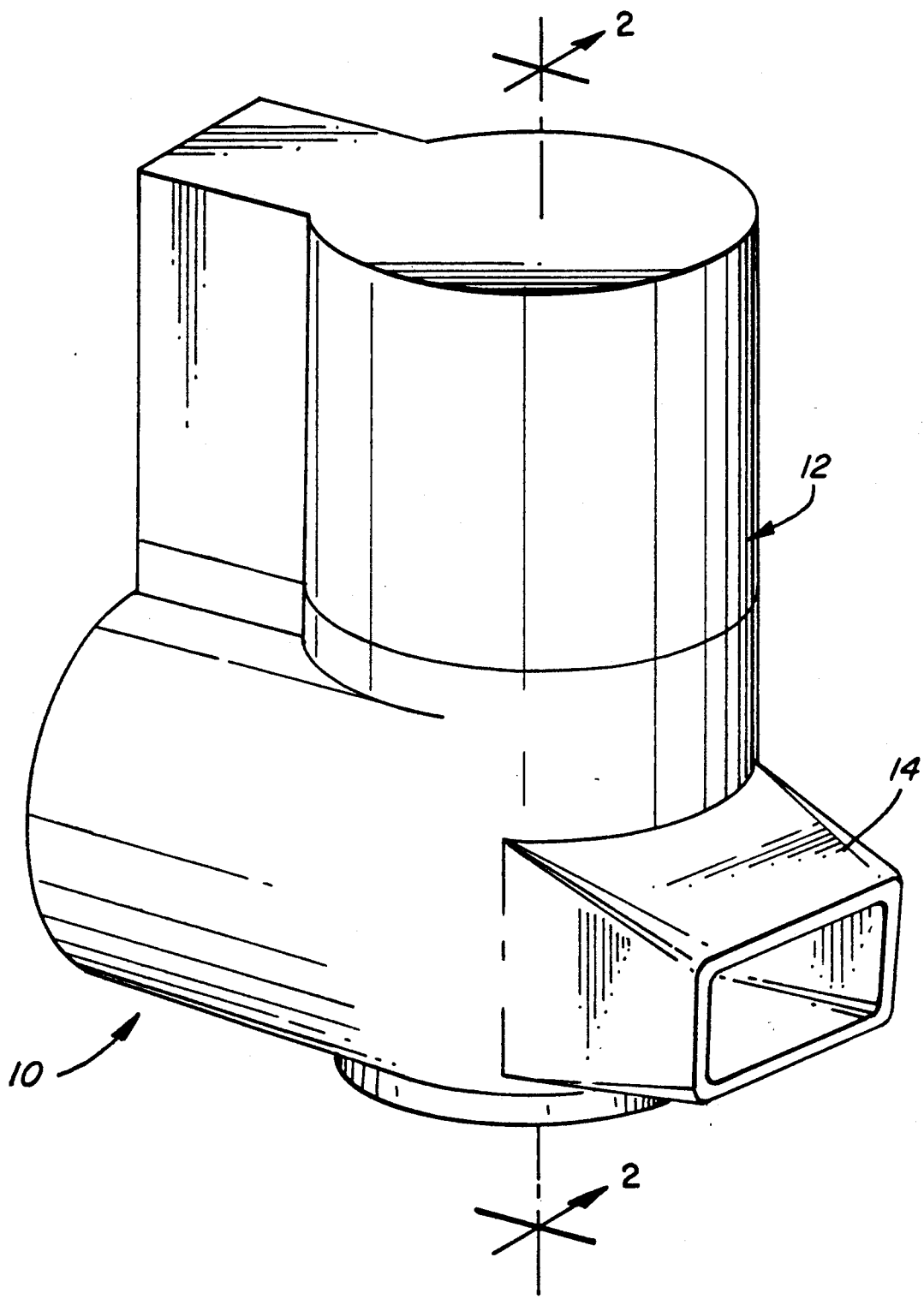
FIG. 1 is a perspective view of the breath-activated inhalation device of the present invention.

Referring now to the drawings in detail wherein like numerals indicate like elements throughout the several views, the breath-activated inhalation device of the present invention is illustrated by the numeral 10.

The device 10 includes a two-piece housing 12 consisting of a cover 13 and a base 15 which may be snapped over cover 13. The assembled housing 12 is generally cylindrical in shape, as illustrated in FIG. 1. The housing base 15 has a lateral extension 14 for insertion in the mouth of a user. A cover 16 can be removed to expose the interior of the extension 14.

The opposite side of the housing includes a flexible diaphragm-type valve 18. Valve 18 is flexible and is pivoted at opposite ends between opposed surfaces 20 and 22 at opposed, spaced portions of housing base 15 and a cap 24. The cap 24 has an opening 26 for receiving a portion of the flexible diaphragm-type valve 18.

Figure 2:
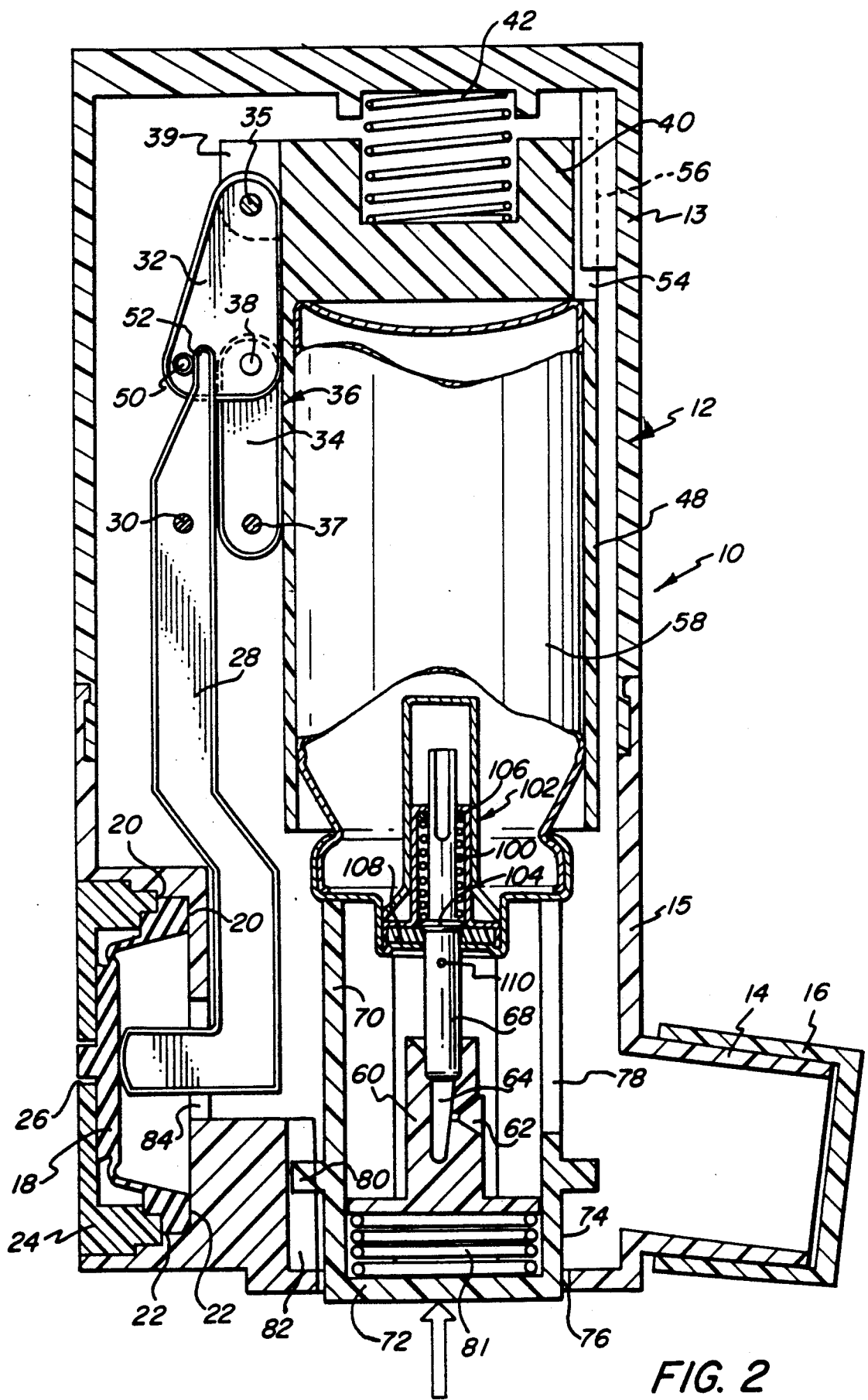
FIG. 2 is a longitudinal cross-sectional view of the breath-activated inhalation device of FIG. 1 substantially taken along the plane indicated by line 2—2 of FIG. 1 and illustrating the device in a cocked condition ready for use.
Figure 3:
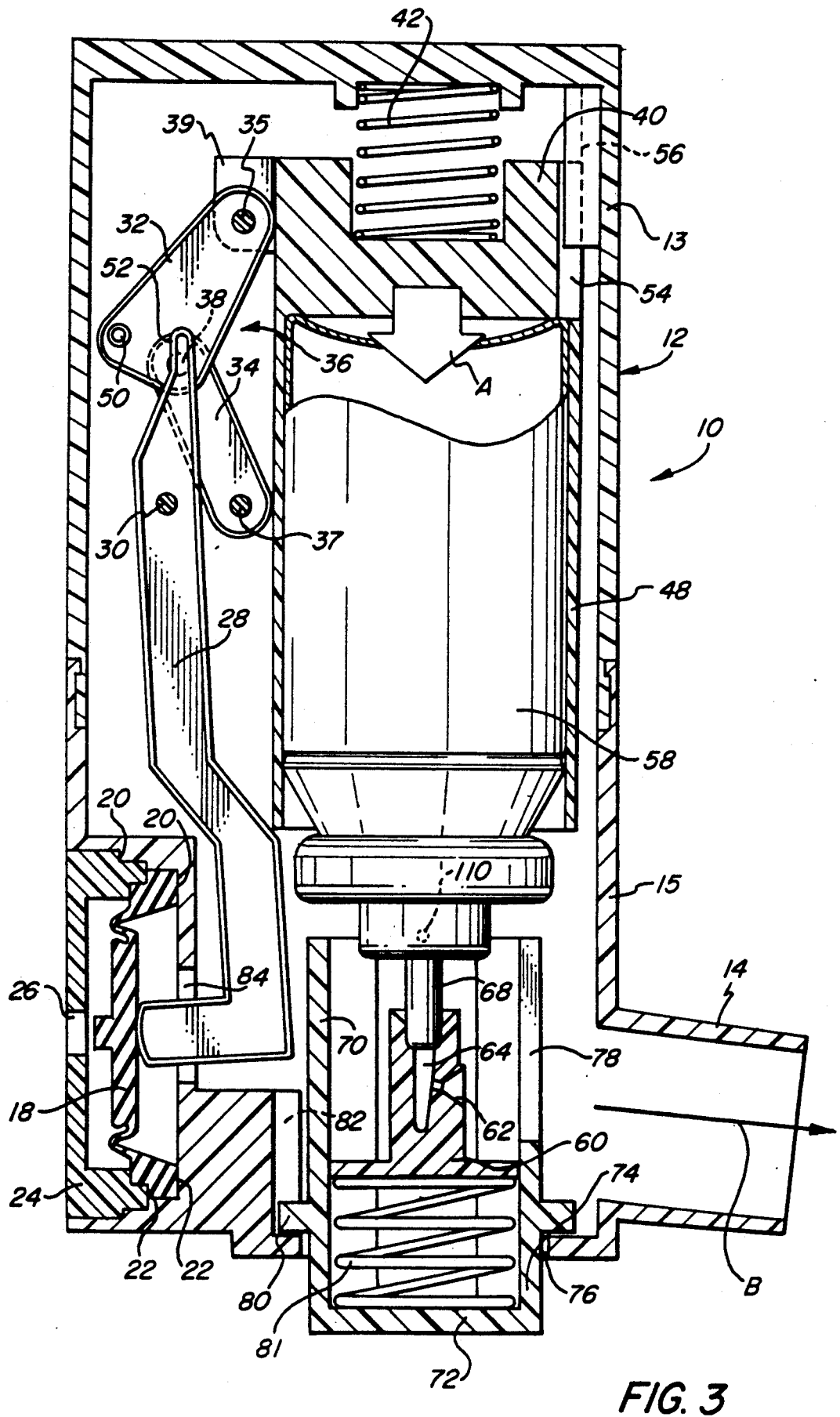
FIG. 3 is a view similar to FIG. 2 indicating the position of the components of the device upon being activated by a user upon inhalation.

The rear surface of the diaphragm-type valve 18 is in contact with a lever or trigger 28 pivotably connected about an axle 30 to an interior surface of housing 12. A pair of arms or links 32,34 of a toggle linkage arrangement 36 are pivoted to each other along the axis 38 on link 34, and are normally in an aligned, linear fashion as illustrated in FIG. 2. Upper arm or link 32 is pivotally connected by an axle 35 to an ear 39 on a block 40, normally biased by a spring 42 downwardly as indicated by arrow A of FIG. 3. Lower arm or link 34 has an axle 37 pivotably mounted on the wall of the cylindrical housing 12. Upper arm or link 34 includes a laterally projecting pin 50 normally in contact with a flat surface 52 on the upper portion of lever 28. Block 40 has an elongated key 54 on a surface opposite from ear 39 received in a keyway or slide 56 on cover portion 13 of housing 12, which keeps block 40 and extension 48 from rotating and serves as a guide for reciprocable, vertical movement of block 40.

A metered dose aerosol container 58 having a medicant is housed within cylindrical extension 48 of block 40. Container 58 is provided with a valve stem 68 seated in a nozzle 60 having a dispensing orifice 62 in communication with the interior of valve stem 68 through a bore 64 in nozzle 60. Nozzle 60 floats and is seated on a coil spring 81 disposed between the base of the nozzle 60 and the interior wall of a pushbutton 72 having a key 80 slidably received in a slot or keyway 82 formed on the interior portion of base 15 of housing 12.

As shown in FIG. 2, the aerosol container valve stem 68 is normally moved downwardly under the urging of a compressed spring 100 held captive in aerosol valve assembly 102, between an enlarged flange 104 on stem 68 and a valve plate 106. The stem 68 slides through a second valve plate 108 disposed in the bottom of valve assembly 102 to position an orifice 110 outside of container 58 to preclude the flow of medicant from the interior of container 58 through orifice 110 and stem 68 into the bore 64 in nozzle 60 and out dispensing orifice 162 into mouthpiece 14.

Container 58 is normally spaced from the top of the annular wall 70 of pushbutton 72 which has a lower portion 74 extending through an opening 76 in the bottom of base portion 15 of housing 12. Annular wall 70 includes an opening 78 in communication with orifice 62 through which medicant can be dispensed and mixed with air drawn into the interior of housing 12. The opposite portion of wall 70 includes the key 80 received in a keyway or slide 82 on the interior portion of base portion 15 of housing 12. Keyway 82 and key 80 prevent pushbutton 72 from rotating and prevents separation of pushbutton 72 from housing 12.

Upon inhalation of air from the interior of housing 12 through mouthpiece 14, flexible diaphragm-type valve 18 exposed through opening 26 to the ambient air surrounding the housing is moved inwardly due to the difference in ambient air pressure to that in the housing to expose the interior of the housing to the ambient air which is then drawn into the housing. Upon movement of the valve 18, it strikes the bottom of lever 28 connected to toggle linkage arrangement 36, causing the lever 28 to pivot about axle 30. Surface 52 on lever 28 strikes pin 50 and breaks the linear locking relationship of links 32,34 illustrated in FIG. 2, causing the links to pivot outwardly to the position illustrated in FIG. 3. This enables coil spring 42 to extend and move block 40 against the rear of the medicant-containing, aerosol valve actuated, bottle 58. The bottle is urged downwardly by the block 40 and moved relative to its aerosol valve stem 68 held captive in seated engagement in bore 64 of floating nozzle 60, opening the valve and dispensing a metered dose of the medicant through orifice 110 now within the bottle, bore 64, orifice 62 and opening 78 to be mixed with the inhaled air in the interior of housing 12, which combination is inhaled by the user, as indicated by arrow B in FIG. 3.

After the bottle 58 has been moved downwardly to open the aerosol valve assembly in bottle 58, the bottle 58 will continue its downward movement until it contacts the top of wall 70, causing the pushbutton 72 to be lowered, if necessary, through opening 76. At the same time, the spring 81 is compressed (FIG. 2) by downward movement of nozzle 60, and then expands (FIG. 3) until the pressure on nozzle 60 is insufficient to overcome the pressure of compressed spring 100 so the stem 68 is extended to close the aerosol valve, establishing the dispensing of only a measured dose of the medicant. The pushbutton 70, now extending exteriorly of the housing 15 through opening 76, can be manually returned upwardly as shown by the arrow in FIG. 2, to recock the device 10, and then the spring 81 returns the pushbutton to its exterior position. Upon recocking device 10, block 40 is moved upwardly to reset the toggle linkage 36 in a linear position to hold the coil spring 42 in a compressed condition until the inhalation cycle is repeated, while pin 50 repivots lever 28 about axle 30 through opening 84 into contact with the rear of diaphragm valve 18 to close the valve.

What is claimed is:

1. A fluid dispensing device comprising:
   a housing having an interior chamber, said interior chamber containing air admitted from the ambient;
   a pressurized medicament container having pressure valve means for dispensing a quantity of medicament;
   nozzle means for mixing medicament with air from said interior chamber, said nozzle means being matingly connectable with said pressure valve means;
   block means for urging said pressurized medicament container into contact with said nozzle means and opening said pressure valve means;
   a mouthpiece extending from said housing and in fluid communication with said interior chamber and said nozzle means;
   a diaphragm valve means for admitting ambient air into said interior chamber, said diaphragm valve means being in fluid communication with the ambient and said interior chamber, said diaphragm valve means having a membrane means for responding to pressure differentials between the ambient and said interior chamber;
   a rotatable lever having a first end, a second end and an axis of rotation, said rotatable lever being within said housing and adapted to contact said membrane means so as to allow displacement of said first end causing rotation of said rotatable lever about said axis of rotation; and
   toggle linkage means for normally locking said block means distal from said nozzle means and upon rotation of said rotatable lever releasing said block means, said second end of said rotatable lever pivotally cooperating with said toggle linkage means.

2. The fluid dispensing device of claim 1 including:
   means on said housing for resetting said toggle linkage means to reposition and lock said block means against movement.

3. The fluid dispensing device of claim 2 wherein said resetting means includes:
reciprocably slidable button means on said housing for contacting said medicament container to push said medicament container upwardly relative to said nozzle means while simultaneously causing said block means to repivot said toggle linkage means to its locking position.

* * * * *